United States Patent [19]

Scates et al.

[11] Patent Number: 5,300,685
[45] Date of Patent: Apr. 5, 1994

[54] REMOVAL OF HALIDE IMPURITIES FROM ORGANIC LIQUIDS

[75] Inventors: Mark O. Scates, Pearland; R. Jay Warner; G. Paull Torrence, both of Corpus Christi, all of Tex.

[73] Assignee: Hoechst Celanese Corporation, Somerville, N.J.

[21] Appl. No.: 799,455

[22] Filed: Nov. 25, 1991

[51] Int. Cl.$^5$ .................. C07C 51/42; B01D 15/04
[52] U.S. Cl. .................. 562/608; 560/248; 210/665; 210/679; 210/683; 210/690
[58] Field of Search .............. 562/608; 210/665, 679, 210/683, 690; 560/248

[56] References Cited

U.S. PATENT DOCUMENTS 4,615,806 10/1986 Hilton .................. 210/690
4,664,753 5/1987 Erpenbach et al. .................. 203/29

FOREIGN PATENT DOCUMENTS 2112394 7/1983 United Kingdom .................. 560/248

Primary Examiner—José G. Dees
Assistant Examiner—Keith MacMillan
Attorney, Agent, or Firm—Donald R. Cassady; Stuart D. Frenkel

[57] ABSTRACT

A method is provided for removing iodide compounds, particularly alkyl iodide compounds, from iodine-containing liquids, particularly carboxylic acids and anhydrides manufactured by the carbonylation of alcohols, ethers, esters, and the like in the presence of a rhodium catalyst and an alkali metal or alkaline earth metal salt, particularly a lithium salt, wherein the carboxylic acid or anhydride is contacted with a silver or mercury salt coordinated to a polymeric resin containing functional groups having the capability to quaternize with or form ionic salts with the alkyl halides.

20 Claims, No Drawings

REMOVAL OF HALIDE IMPURITIES FROM ORGANIC LIQUIDS

BACKGROUND OF THE INVENTION

The present invention relates to the removal of halide impurities from halide contaminated liquids. The invention is particularly effective in removing halide impurities from halide containing organic liquids such as the reaction products of carbonylation processes.

Carbonylation is a process used to manufacture a variety of commercially important chemicals. Such chemicals include carboxylic acids, carboxylic acid anhydrides, acetic anhydride, propionic acid, and glyoxylic acid. A particularly important carboxylic acid produced by carbonylation is acetic acid. The chemical industry manufactures millions of tons of acetic acid each year for use in the manufacture of a variety of other useful chemicals such as vinyl acetate and cellulose acetate. For example, vinyl acetate is the raw material for polyvinyl acetate, a thermoplastic used in the manufacture of adhesives, water based paints and latex paints. Cellulose acetate is used in the manufacture of a variety of products such as plastic fibers, films and sheets. The following illustrates the general reaction for the carbonylation of methanol with carbon monoxide to form acetic acid:

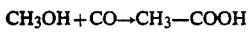

Carbonylation processes typically employ metal catalysts such as cobalt, nickel or rhodium in a liquid reaction medium. For example, in the carbonylation of methanol to make acetic acid, rhodium is generally employed as the catalyst by contacting the reactants with rhodium in the reaction medium. Typically contact is achieved by dissolving the rhodium in the reaction medium.

The reaction medium is generally an organic solution containing the starting materials and the catalyst. In addition, halogen-containing catalyst promoters are typically employed in these reaction systems. Alkyl halides are common promoters. Alkyl iodides, most notably methyl iodide, are typically employed as promoters in acetic acid production. For the rhodium catalyzed acetic acid synthesis, the active species is believed to be $[Rh(CO)_2I_2]^-$. In addition, iodide salts, such as sodium iodide, potassium iodide, or lithium iodide or mixtures thereof, can be added to the reaction medium as co-promoters or catalyst stabilizers. The result is a halide-rich reaction mixture.

Although halide promoters and stabilizers such as methyl iodide and $I^-$ salts improve the efficiency and productivity of carbonylation processes, the continued presence of halide compounds in the carbonylation reaction products is undesirable. It is customary that, even after extensive purification, carbonylation reaction products typically contain contaminants from the original halide compounds added to the reaction medium prior to the carbonylation reaction and new halide compounds generated during the carbonylation reaction. For example, in the carbonylation of methanol with carbon monoxide using methyl iodide and lithium iodide, the carbonylation reaction products contain a variety of iodide compounds, including methyl iodide and hexyl iodide. These halides must be removed from the carbonylation product. The desired carbonylation product, such as acetic acid, is often a starting material in a subsequent process employing a halide-sensitive catalyst. For example, about 75% of the acetic acid produced is used in the production of vinyl acetate and cellulose acetate by processes using sensitive, expensive catalysts containing metals such as gold and palladium. Since halides, especially iodide compounds, deactivate or "poison" gold and palladium catalysts, starting materials that are essentially halide-free are required. The industry standard for halide contaminants in acetic acid is 10 parts per billion (ppb) or less. However, poisoning effects on precious metal catalyst are generally cumulative and irreversible as in the case of iodide contamination of catalysts for vinyl acetate production. Consequently, less than 1 ppb halide content is desired.

The problems associated with halide impurities in organic liquids have prompted the search for several solutions for removing the impurities. One method for removing halide impurities is a distillation process using peracids such as potassium permanganate to fix the iodide prior to distillation. Other methods involve the use of liquid-phase extraction processes with non-aromatic hydrocarbons such as alkanes and cycloalkanes.

A number of methods are directed to treating carbonylation reaction products with reagents that form iodide salts. For example, many organo-nitrogen, organo-phosphorous and organo-sulfur species are known to quaternize, or form ionic salts, with alkyl halides such as methyl iodide and hexyl iodide. One specific example is the reaction of trialkyl, or the more stable triaryl, phosphines with methyl iodide:

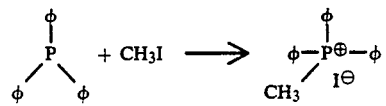

Similarly, dialkyl or diaryl sulfides and dialkyl or diaryl sulfoxides generally react with methyl iodide as follows:

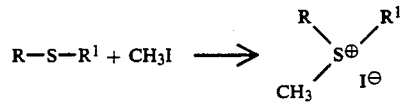

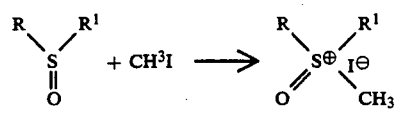

Heterocyclic and tertiary amines react with methyl iodide as follows:

wherein Y represents the remaining portion of the hetero molecule.

The resulting salt can be more easily separated from the solution than the $CH_3I$ itself. The purified carbonylation product is collected by distillation. However, these compounds have not demonstrated the level of halide removal efficiency demanded by the industry.

One approach to enhancing the halide removal capability of quaternizing compounds such as alkyl or aryl phosphines or heterocyclic aromatic nitrogen compounds is described in U.S. Pat. No. 4,664,753, incorporated herein by reference. The iodide removal approach described involves a homogeneous system wherein iodide contaminates contained in the carbonylation reaction products are treated with a combination of alkyl or aryl phosphines or a heterocyclic aromatic nitrogen compound and at least one of the metals copper, silver, zinc or cadmium, or metal salts thereof, such as copper (II) acetate or silver acetate, to fix the iodide in a non-volatile form. A second step is required to remove the iodide from the carbonylation products. In the second step, the carbonylation products are separated from the fixed iodide by distillation of the carbonylation products. Since a stoichiometric excess of metal and phosphine or aromatic nitrogen compound is required to achieve substantially complete iodide removal, this homogeneous system requires recovery and disposal of toxic metal residues. Furthermore, the distillation required to separate the carbonylation product from the halide precipitate is an additional step in the production process, increasing its duration and expense.

Another approach suggests avoiding the combination of alkyl and aryl phosphines or aromatic nitrogen compounds and metals or metal salts. This approach suggests treating carboxylic acid or carboxylic acid anhydrides with an unsupported silver salt "scavenger," e.g., silver acetate, in the absence of alkyl or aryl phosphines and heterocyclic aromatic nitrogen compounds. A high stoichiometric excess of metal salt to the halide impurities is required to achieve significant halide removal. Also, as in the treatment/precipitation procedures described, an additional distillation step is required to purify the carbonylation product. Moreover, the scavenger residue must be recovered. In addition, the process does not achieve sufficient halide removal for demanding end uses such as vinyl acetate production.

A particularly effective approach which avoids many of the problems associated with distillation and extraction processes employs a strong acid cation exchange resin. One such resin is a sulfonated copolymer of styrene and divinyl benzene in which at least a portion of the active sites are exchanged to the silver or mercury form through the exchange of a silver or mercury salt, such as silver acetate or mercuric acetate. In this process, the silver or mercury exchanged resin can be placed in a column and the halide contaminated liquid passed through the column. Greater than 99.99% removal of iodide compounds from iodide contaminated acetic acid can be achieved through this process as reported in U.S. Pat. No. 4,615,806, incorporated herein by reference.

Although each of these approaches offer various degrees of halide removal effectiveness and commercial feasibility, still other effective, efficient, and commercially desirable halide impurity removal processes are desired.

SUMMARY OF THE INVENTION

The present invention provides an efficient one-step heterogeneous halide removal process. Rather than employing resins having a strong acid cation exchange functionality, the present invention employs a polymeric resin having functional groups capable of forming both coordination complexes with metal salts such as silver or mercuric acetate and the capability to quaternize or form ionic salts with alkyl halides. The polymeric resin coordinated with the metal salt is contacted with a liquid containing halide impurities. Halide containing liquids include liquid or vaporous organic materials such as carbonylation reaction products. Halide impurities are fixed in the form of precipitated metal halides trapped in the polymeric resin matrix. The coordinated polymeric resin can be employed in a fixed bed process wherein feedstock is continuously passed through the resin bed for removal of halide contaminants. Consequently, one particular advantage of the present invention is the ability to trap the metal halide within the resin matrix in one step. This ability obviates a subsequent distillation step required to separate the metal halide and excess reagents from the liquid. Moreover, the recovery and disposal of toxic residues is simplified. Of particular importance and value is the use of the present invention to remove iodine values from acetic acid, acetic anhydride, and mixtures thereof manufactured by the carbonylation of methanol in the presence of alkyl iodides and alkali metal iodides, i.e., lithium iodide.

DETAILED DESCRIPTION OF PREFERRED EMBODIMENTS

The present invention employs polymeric resins coordinated with metal salts which react with and precipitate halide impurities from halide contaminated liquids. One particular advantage of the present process is the ability to fix the halide impurity and trap the impurity within the resin matrix to effectively remove the impurity in a single step, thus avoiding additional distillation and recovery steps to separate fixed halide impurities from the halide containing liquid.

The characteristics of polymers useful in the practice of this invention are polymers having functional groups capable of forming coordination complexes with metal salts such as silver or mercury salts. These functional groups also are characterized by the presence of an unshared electron pair that can participate in nucleophilic substitution reactions with alkyl halides such as methyl iodide. Examples of such functional groups are phosphines, sulfides, sulfoxides, amines, arsines, and sulfur or nitrogen containing heterocyclics. Specific polymer examples that are believed to be most effective in the practice of this invention include polymers such as poly-4-vinyl pyridine (PVP), polyphenylene sulfide (PPS) and polybenzimidazole (PBI).

The resin is prepared by immersing polymer with a metal salt in a suitable solvent. "Solvent" as used herein refers to a solvent for the metal salt. The immersed polymer is mixed with the metal salt solution. The metal salts useful in practicing the invention are generally salts of transition metals which can coordinate with the polymeric resin functional group. In addition, the desirability of the metal salt is governed by the insolubility of the metal halide formed in the particular liquid. General, but non-limiting examples of metals salts include silver, mercury, copper, and lead salts sufficiently soluble in the solvent to allow coordination with the resin. Examples of particularly preferred metal salts include silver or mercury salts such as silver acetate, silver nitrate or mercuric acetate. The metal salt forms a coordination complex, rather than an ionic bond, with the resin functional group. The solvent containing the uncoordinated salt is removed from the resin and the resin is preferably washed with pure liquid from which the halide moiety is to be removed prior to its use. The resin coordinated with the metal salt is then contacted with the liquid containing the halide impurity.

Typically the resin is packed into a column as for example by pouring a slurry of the resin into the column to an appropriate height. The iodide containing liquid is then passed continuously through the column contacting the resin for a sufficient time to effect removal of the iodide. Alternatively, the iodide containing solution is allowed to contact the resin in a batch operation.

The coordination between the metal salt and the polymer functional group can be performed in any suitable inert solvent. The solvent can include the liquid from which the iodide will be removed according to the method of this invention, such as acetic acid, $H_2O$, acetic acid/$H_2O$ mixtures, acetic anhydride, or acetic acid/acetic anhydride mixtures. The solvent may also include methanol, methyl acetate, and other solvents for the metal salt. Preferably the polymeric resin is first conditioned in the solvent by immersing the polymer in the solvent to form a mixture or slurry and applying a vacuum on the head space above the polymer-solvent mixture to facilitate removal of trapped gases such as air in the polymer matrix and to allow the solvent to flow more easily into the resin matrix. After the resin is conditioned in the solvent, the metal salt or a solution of the metal salt is added to the conditioned polymer mixture or slurry. The metal salt solution can be a solution of the metal salt in the solvent used to prepare the resin or another compatible solvent. The mixture or slurry is then stirred and heated as necessary to allow the metal salt to coordinate with the resin's functional groups. The mixture of metal coordinated resin and solvent is then cooled, filtered and washed with additional solvent.

As discussed hereinabove, the metal coordinated resin can be contacted with the halide containing liquids or vapor in any suitable manner. The resin can be employed in a fixed-bed system and halide containing liquid passed through the resin bed to remove halide impurities. Alternatively, halide containing vapors could be passed through a column containing the resin. No special processing parameters are contemplated. For example, room temperature would be an adequate processing temperature, although elevated temperatures should allow reduced residence time in the resin bed. The upper temperature limit is determined by the thermal stability of the polymer. Since operation at elevated temperatures is desirable in many carbonylation processes, the thermal stability of polymers useful in the present invention is advantageous. For example, acetic acid residues and distillates generally must be cooled prior to passing the acetic acid through a fixed bed of silver exchanged sulfonated styrene/divinyl benzene copolymer to avoid desulfonation of the resin. Polymers useful in the present invention, such as poly-4-vinyl pyridine have a higher thermal stability which permits passing the residue through the fixed bed without cooling. For example, Reillex TM 425 has an upper temperature range of about 260° C. Moreover, the present invention allows a potentially higher silver loading on the resin, resulting in increased bed life or iodide removal capacity. Likewise, the system pressure should not be a significant factor in the application of the present invention. The metal halide "precipitate" generated by contacting the metal coordinated resin with the halide-containing process stream is apparently trapped within the matrix of the resin.

The following examples further illustrate the practice of the present invention. The examples demonstrate that the resulting carbonylation product has an acceptable level of halide impurity. No distillation step is required.

EXAMPLES

Example 1: Resin Preparation

Poly-4-vinyl pyridine (Reillex TM 425 available from Reilly Industries, Inc., Indianapolis, Ind.) was coordinated with silver nitrate using $H_2O$ as the solvent. The poly-4-vinyl pyridine resin was conditioned in the solvent by immersing about 200 cubic centimeters (cc) of the polymer in about 300 cc of $H_2O$ and applying a vacuum to the head space above the polymer-$H_2O$ mixture to facilitate removal of trapped air in the polymer matrix and to allow the $H_2O$ to flow more easily into the pores of the resin. After the resin was conditioned in the $H_2O$, a solution of silver nitrate in the $H_2O$ was added to the polymer-solvent mixture. The mixture was stirred using a magnetic stirrer and heated on a hot plate while stirring to allow the silver nitrate to coordinate with the resin's functional groups. The mixture of resin, solvent, and silver nitrate was maintained at about 80° C. while stirring for two hours. The resin slurry was then cooled, filtered and washed with $H_2O$ to obtain a silver-coordinated form of the polymer in $H_2O$.

Additional polymers were similarly prepared as follows:

| Polymer | Metal Salt | Solvent |
| --- | --- | --- |
| Reillex TM 425 | silver acetate | acetic acid |
| Polyphenylene Sulfide (PPS) | silver acetate | acetic acid |
| Polybenzimidazole (PBI) | silver acetate/ silver nitrate | acetic acid/ $H_2O$ |

Example 2: Comparative Polymer Preparations

Samples of Reillex TM 425, PPS and PBI were conditioned in acetic acid generally as described in Example 1 by immersing the polymers in the acetic acid and applying a vacuum to the head space above the polymer/solvent mixture to remove trapped air and facilitate the flow of the solvent into the polymer matrix. No metal salts were added.

Example 3; Batch Testing of Resins 20 cc of each resin prepared as in Example 1 were mixed with 80 cc of acetic acid in 4 oz. bottles. The acetic acid was spiked with hexyl iodide to obtain a total iodide content of 504 parts per million (ppm). The capped bottles were placed on a wrist shaker and agitated for two hours at room temperature.

20 cc of the comparative polymer samples in the acetic acid solvent were mixed with 80 cc of acetic acid containing hexyl iodide at a 504 ppm total iodide level. The comparative examples were agitated on the wrist shaker for two hours at room temperature.

A sample of Ag+ as Ag acetate was also prepared by mixing 10 grams of Ag acetate in 80 cc of acetic acid containing hexyl iodide at a 504 ppm total iodide level. In addition a sample of silver exchanged on a sulfonated styrene/divinyl benzene copolymer (Amberlyst TM 15), generally as described in U.S. Pat. No. 4,615,806, was prepared by immersing the silver exchanged resin in acetic acid containing hexyl iodide at a 504 ppm total iodide level. The silver salt and silver exchanged resin samples were agitated on a wrist shaker for two hours at room temperature. After agitation, each sample was allowed to settle and the treated acetic acid decanted from the containers. The results of the hexyl iodide removal tests are set forth in Table I.

TABLE I

| TEST MATERIAL | FEED HEXYL IODIDE (PPB) | PRODUCT HEXYL IODIDE (PPB) | HEXYL IODIDE REMOVED (%) |
|---|---|---|---|
| Ag+ as AgAc | 504,000 | 439,000 | 13% |
| Reillex TM 425 | 504,000 | 291,000 | 42% |
| PPS | 504,000 | 516,000* | 0% |
| PBI | 504,000 | 360,000 | 29% |
| Reillex TM 425/ AgNO$_3$ (H$_2$O prep) | 504,000 | <1 | 100% |
| Reillex TM 425/ AgAc (acetic acid prep) | 504,000 | <1 | 100% |
| PPS/AgAc (acetic acid prep) | 504,000 | <1 | 100% |
| PBI/AgAc/ AgNO$_3$ (acetic acid/ H$_2$O prep) | 504,000 | <1 | 100% |
| Silver Exchanged Resin | 504,000 | <1 | 100% |

*Result attributed to analytical variability.

Analysis of the treated samples was conducted by gas chromatography using an electron capture detector. The detection limit for the hexyl iodide was approximately 1 ppb. Samples that had high hexyl iodide concentrations after treatment (>50 ppb) were diluted with iodide-free acetic acid before analysis to make the resulting hexyl iodide <50 ppb to maintain linearity of the analysis. The results were then multiplied by the appropriate dilution factor.

To further ascertain the iodide removal efficiency of the silver treated resins and the silver exchanged resin the samples were further analyzed for total iodide removal. The results of the total iodide removal test are set forth below in Table II.

TABLE II

| Test Material | Product Total Iodide* | Total Iodide Removed (%) |
|---|---|---|
| Reillex TM 425/ AgNO$_3$ (H$_2$O Prep) | 959 | >99.8% |
| Reillex TM 425/ AgAc (Acetic Acid Prep) | <1 | >99.9% |
| PPS/AgAc (Acetic Acid Prep) | 49 | >99.9% |
| PBI/AgAc/AgNO$_3$ (Acetic Acid/ H$_2$O Prep) | 64 | >99.9% |
| Silver Exchanged Resin | <1 | >99.9% |

*Total iodide as I. The hexyl iodide and total iodide were both measured on an iodide basis analyzing the atomic weight of iodide.

As indicated, the data shows that silver alone or non-metal salt coordinated Reillex TM 425, PPI or PPS are relatively ineffective for alkyl iodide removal. The metal salt coordinated resins were extremely effective at removing alkyl iodide from acetic acid.

Example 4: Batch Test of Triphenylphosphine on Polystyrene

A triphenylphosphine reagent adsorbed on polystyrene cross-linked with 2% divinylbenzene was coordinated with silver nitrate/silver acetate in a H$_2$O/HAc mixture following the procedure described in Example 1. The triphenylphosphine/polystyrene polymer was obtained from Aldrich Chemical Co., Inc., Milwaukee, Wisc. A batch test following the procedure set forth in Example 3 was performed using the triphenylphosphine adsorbed on polystyrene. The resulting liquid phase was turbid with suspended, untrapped AgI. Thus, the quaternizable reactive reagent must be chemically bonded to the polymer backbone for effective one-step iodide removal.

Example 5: Fixed Bed Continuous Run

A silver salt coordinated resin was prepared by adding 350 grams of water to 245 grams of Reillex TM 425 polyvinyl pyridine resin and evacuating the mixture to degas the resin. After soaking the mixture under the vacuum for 20 minutes, the following components were added:

(a) 50 grams glacial acetic acid
(b) 5.0 grams silver acetate
(c) 100.3 grams silver nitrate
(d) 46.7 grams concentrated nitric acid The resulting slurry was stirred on a hot plate for 2 hours at about 80° C.

After cooling, the resin was filtered from the liquid and washed with cold water (20° C.) followed by washing with acetic acid. The washed resin was slurried in acetic acid and the mixture evacuated for 20 minutes. Part of the resin slurry was loaded into a 0.75 inch ID glass column to obtain a 100 cc fixed bed of resin. The excess of acetic acid was drained until the resin bed was covered by 1.0 inch of acetic acid in the column. 500 cc of room temperature acetic acid containing hexyl iodide at a 504 ppm total iodide level were fed through the column (downflow) at 10 cc/minute (6 bed volumes/hour). A sample of the eluant was taken after 5 bed volumes had been processed through the resin column and analyzed for iodide content. An additional 100 cc of the room temperature hexyl iodide feed was processed through the column at a flow rate of 1 cc/minute (100 minutes of residence time; 0.6 bed volumes/hour), and a sample of the eluant obtained. Both samples were analyzed for total iodide content and the results are set forth below in Table III.

TABLE III

| RESIDENCE TIME (MINUTES) | PRODUCT TOTAL IODIDE CONTENT (PPM) | TOTAL IODIDE REMOVAL (%) |
|---|---|---|
| 10 | 124 | ~75 |
| 100 | 8 | >98 |

As stated, many of the polymers useful in the present invention are stable at elevated temperatures. Accordingly, the advantage of high thermal stability can be used to reduce the required residence time by passing the feed through the resin bed at elevated temperatures.

What is claimed is:

1. A method of removing halides from halide-containing liquids in liquid or vapor form, comprising (a) contacting a halide-containing liquid or vapor with a polymeric resin having functional groups forming coordination complexes with one or more metal salts capable of reacting with halides to form metal halide precipitates in the halide-containing liquid or vapor, said functional groups having the capability to quaternize or form ionic salts with alkyl halides, and (b) maintaining the contact between the liquid or vapor and the coordinated resin for a time sufficient for metal halide precipitates to form and trapping said precipitates in the matrix of said polymeric resin.

2. The method of claim 1 wherein said polymeric resins have functional groups selected from the group consisting of phosphines, sulfides, sulfoxides, amines, arsines, and sulphur or nitrogen-containing heterocycles.

3. The method of claim 1 wherein said polymeric resin is selected from the group consisting of poly-4-vinyl pyridine, polyphenylene sulfide, and polybenzimidazole.

4. The method of claim 1 wherein said metal salts are salts of metals selected from the group consisting of silver, mercury, copper and lead.

5. The method of claim 4 wherein the metal salt is selected from the group consisting of silver acetate, silver nitrate and mercuric acetate.

6. The method of claim 1 wherein said halide-containing liquid comprises a halide-containing solution of acetic acid, acetic anhydride, or mixture thereof.

7. The method of claim 1 wherein said halide is an alkyl iodide.

8. The method of claim 1 wherein said coordinated resin is contacted with said liquid or vapor by passing said liquid or vapor through a bed of said coordinated resin.

9. A method of removing halides from halide-containing liquids in liquid or vapor form, comprising (a) contacting the halide-containing liquid or vapor with a polymeric resin having functional groups selected from the group consisting of phosphines, sulfides, sulfoxides, amines, arsines, and sulfur or nitrogen-containing heterocycles, said functional groups in the form of coordination complexes with one or more silver, mercury, copper, or lead salts, and (b) maintaining the contact between the liquid or vapor and the coordinated resin for a time sufficient for metal halide precipitates to form.

10. The method of claim 9 wherein said polymeric resin is selected from the group consisting of poly-4-vinyl pyridine, polyphenylene sulfide, and polybenzimidazole.

11. The method of claim 9 wherein the metal salt is selected from the group consisting of silver acetate, silver nitrate and mercuric acetate.

12. The method of claim 9 wherein said halide-containing liquid or vapor comprises a halide-containing solution of acetic acid, acetic anhydride, or mixture thereof.

13. The method of claim 9 wherein said halide is an alkyl iodide.

14. The method of claim 9 wherein said coordinated resin is contacted with said liquid by passing said liquid or vapor through a bed of said coordinated resin.

15. A method of removing iodide compounds from an iodide-containing solution of acetic acid, acetic anhydride, or mixture thereof comprising (a) contacting the iodide-containing acetic solution with a polymeric resin having functional groups selected from the group consisting of phosphines, sulfides, sulfoxides, amines, arsines, and sulfur or nitrogen-containing heterocycles, said functional groups forming coordination complexes with one or more metal salts of silver, mercury, copper or lead, and (b) maintaining the contact between the solution and the coordinated resin for a time sufficient for metal iodide precipitates to form.

16. The method of claim 15 wherein said polymeric resin is selected from the group consisting of poly-4-vinyl pyridine, polyphenylene sulfide, and polybenzimidazole.

17. The method of claim 15 wherein the metal salt is selected from the group consisting of silver acetate, silver nitrate and mercuric acetate.

18. The method of claim 15 wherein said coordinated resin is contacted with said solution by passing said solution through a bed of said coordinated resin.

19. The method of claim 15 wherein said iodide compounds are alkyl iodides.

20. The method of claim 19 wherein said alkyl iodides comprise methyl iodide, hexyl iodide or mixtures thereof.

* * * * *